(12) United States Patent
Deutsch

(10) Patent No.: US 6,933,152 B1
(45) Date of Patent: Aug. 23, 2005

(54) ARTIFICIAL HUMAN FECES

(75) Inventor: Marshall E. Deutsch, Sudbury, MA (US)

(73) Assignee: NERL Diagnostics, East Providence, RI (US)

( * ) Notice: Subject to any disclaimer, the term of this patent is extended or adjusted under 35 U.S.C. 154(b) by 0 days.

(21) Appl. No.: 10/814,444

(22) Filed: Mar. 31, 2004

Related U.S. Application Data

(60) Provisional application No. 60/460,313, filed on Apr. 4, 2003.

(51) Int. Cl.⁷ .............................................. G01N 33/72
(52) U.S. Cl. .............................. 436/66; 436/8; 436/15; 436/18; 252/408.1
(58) Field of Search ................................ 436/8, 15, 18, 436/66; 252/408.1

(56) References Cited

U.S. PATENT DOCUMENTS 4,394,452 A * 7/1983 Hartl et al. .................... 436/66
5,356,626 A * 10/1994 Yeo et al. .................... 424/738
5,919,136 A * 7/1999 Rao et al. .................... 600/431

FOREIGN PATENT DOCUMENTS

| JP | 10-319022 | * 12/1998 |
| WO | 94/29385 | * 12/1994 |

OTHER PUBLICATIONS

Kubiak et al. Pediatrics, vol. 91, No. 3, Mar. 1993, pp. 632-636.*
Roanne R. E. Selinger, MD; Sharon Norman, MBA, MT; Jason A. Dominitz, MD, MHS;Failure of Health Care Professionals to Interpret Fecal Occult Blood Tests Accurately; The American Journal of Medicine; Jan., 2003; pp. 64-67; vol. 114; University of California; San Francisco, CA USA.

* cited by examiner

Primary Examiner—Maureen M. Wallenhorst
(74) Attorney, Agent, or Firm—William Nitkin

(57) ABSTRACT

An artificial mixture which simulates human feces and its method of use for fecal occult blood testing as a control material or for proficiency testing are disclosed.

13 Claims, No Drawings

_US 6,933,152 B1_

ARTIFICIAL HUMAN FECES

This application claims priority and benefit of a provisional patent application entitled Artificial Human Feces, Ser. No. 60/460,313 filed Apr. 4, 2003, now abandoned.

BACKGROUND OF THE INVENTION

1. Field of the Invention

This invention relates to quality control and proficiency testing of occult blood, and more particularly relates to providing a control material for testing for occult blood in human feces.

2. History of the Prior Art

Controls are frequently used in testing as an established procedure in the prior art, but are not part of fecal occult blood testing procedures which can have significant error rates. (See Selinger, Roanne R. E., Norman, Sharon and Dominitz, Jason A. Failure of Health Care Professionals to Interpret Fecal Occult Blood Tests Accurately. _The American Journal of Medicine_, January 2003, Vol. 114, pages 64–67) It is important to improve occult blood test accuracy as such tests are used for colorectal cancer screening.

SUMMARY OF THE INVENTION

A method of preparing and using an artificial mixture which simulates human feces is disclosed which mixture can be prepared with or without constituents which give a positive test for occult hemoglobin, thus making it useful as a control material or for proficiency testing in which laboratories are furnished with samples of unknown composition to test their ability to detect analytes of interest.

DESCRIPTION OF THE PREFERRED EMBODIMENT(S)

The basic mixture of this invention which simulates the appearance and texture of human feces can be prepared as follows: to an aqueous base are added at least one thickening agent such as polysaccharides (e.g., starch), polypeptides (e.g., gelatin), and vegetable gums (e.g., guar gum); at least one stabilizer to prevent syneresis (e.g., pyrogenic silica); at least one preservative to resist bacterial or fungal attack (e.g., antibiotics or sodium azide); at least one coloring agent to mimic the color of human feces (e.g., burnt sienna and burnt umber); an acid or base (e.g., sodium bicarbonate or hydrochloric acid) to facilitate the solution of any ingredients which require such facilitation; and, if desired, at least one odorant to mimic the appropriate odor (e.g., indole and skatole).

However, it is not so simple to prepare artificial feces which give an appropriately intense positive test for occult hemoglobin with any of the commonly available tests for this purpose which tests are on the market. Some tests depend solely on the fact that hemoglobin acts as a peroxidase, and provide the appropriate reagents to develop a color from this peroxidase reaction if the feces contain an amount of hemoglobin (from food, or the normal amount of intestinal bleeding which occurs in an individual who does not suffer from pathological amounts of intestinal bleeding). Other tests specifically detect human hemoglobin by means of its reaction with an antibody which reacts less or not at all with hemoglobin from other species. They are much more sensitive than the former type, more than making up for the fact that they fail to react with hemoglobin originating from dietary meat.

Satisfactory results are obtained with both types of occult hemoglobin tests by adding to the artificial series a mixture of non-human and human hemoglobins in a ratio of from 2.5:1 to 7.5:1. In a preferred embodiment of this invention the following materials are dissolved or suspended in one liter of water to make synthetic feces which do not give a positive test for occult blood:

Sodium Azide 5 g
Burnt Sienna Acrylic Color 6.375 g
Burnt Umber Acrylic Color 5.375 g
Gelatin 4.175 g
Pyrogenic Silica 166.8 ml
Corn Starch 150 g To make a preparation which gives a positive test for occult blood, a similar mixture is made, but with the addition of:

Human Hemoglobin 0.333 g
Bovine Hemoglobin 1.688 g
plus 100 mg of sodium bicarbonate to facilitate the dissolution of the hemoglobin.

Thus this invention includes:

(1) Compositions for use in quality control or in proficiency testing of occult-blood tests, comprising a constituent or constituents which act as a peroxidase and one or more of thickening agents, stabilizers, coloring agents, odorants and preservatives in an aqueous base.

(2) Such compositions, in which the peroxidase-acting constituents consist of one part human hemoglobin to 2.5–7.5 parts of other peroxidase-acting constituents.

(3) Such compositions, in which the peroxidase-acting constituents consist of one part of human hemoglobin to 2.5–7.5 parts of non-human hemoglobin.

Although the present invention has been described with reference to particular embodiments, it will be apparent to those skilled in the art that variations and modifications can be substituted therefor without departing from the principles and spirit of the invention.

I claim:

1. A method for quality and proficiency control in fecal blood testing, comprising the steps of:

providing an artificial mixture comprising non-human peroxidase-acting constituents simulating human feces for testing that provides a positive test for occult hemoglobin;

testing such mixture along with other feces samples for occult blood; and utilizing said artificial mixture as a control material when testing such feces samples.

2. The method of claim 1 wherein said artificial mixture further simulates the appearance, texture or odor, or any combination thereof, of human feces.

3. A composition for use in performing a fecal blood test as a quality control and proficiency test, said composition comprising:

artificial feces, said artificial feces comprising:
an aqueous base;
a thickening agent;
a stabilizer;
a preservative; and
a peroxidase mixture comprising at least a non-human peroxidase-acting constituent, said composition yielding a positive test result in a fecal blood test.

4. The composition of claim 3 further comprising a coloring agent and/or an odorant.

5. The composition of claim 3 further comprising human hemoglobin in a ratio of 1 part of said human hemoglobin to 2.5–7.5 parts of said non-human peroxidase-acting constituent.

6. The composition of claim 3 further comprising sodium bicarbonate.

7. The composition of claim 3 wherein said non-human peroxidase-acting constituent comprises non-human hemoglobin.

8. The composition of claim 3 wherein said non-human peroxidase-acting constituent comprises bovine hemoglobin.

9. A composition for use in quality control and proficiency testing of fecal occult blood tests, comprising:
  artificial feces, said artificial feces including:
    an aqueous base material;
    a thickening agent;
    at least one stabilizing agent;
    at least one preservative;
    optionally, at least one coloring agent;
    optionally, at least one odorant; and
  further including a peroxidase-acting constituent consisting of 1 part human hemoglobin to 2.5–7.5 parts other peroxidase-acting constituents for yielding a positive test result for fecal occult blood.

10. The composition of claim 9 wherein said other peroxidase-acting constituents consist of non-human hemoglobin.

11. The composition of claim 9 further comprising sodium bicarbonate.

12. The composition of claim 9 wherein said other peroxidase-acting constituents comprise bovine hemoglobin.

13. A composition for yielding a negative test result in a fecal occult blood test comprising:
  an aqueous base comprising 1 liter of water;
  thickening agents selected from the group consisting of polysaccharides, polypeptides and vegetable gums;
  at least one stabilizer for preventing syneresis;
  at least one preservative for providing resistance to bacterial and fungal attacks;
  at least one coloring agent for mimicking the color of human feces;
  optionally at least one odorant for mimicking the odor of human feces;
  wherein said polysaccharide is 150 grams cornstarch, said polypeptide is 4.175 grams gelatin, said stabilizer is 166.8 ml pyrogenic silica; said coloring agents are 6.375 grams burnt sienna acrylic color and 5.375 grams burnt umber acrylic color, and said preservative is 5 grams sodium azide.

* * * * *